United States Patent
Karnieli et al.

(10) Patent No.: US 12,252,684 B2
(45) Date of Patent: *Mar. 18, 2025

(54) DEVICE AND METHOD FOR CONTROLLING A BIOREACTOR

(71) Applicant: ADVA Biotechnology Ltd., Kiryat Tivon (IL)

(72) Inventors: Ohad Karnieli, Kiryat Tivon (IL); Noam Bercovich, Haifa (IL)

(73) Assignee: ADVA Biotechnology Ltd., Kiryat Tivon (IL)

( * ) Notice: Subject to any disclaimer, the term of this patent is extended or adjusted under 35 U.S.C. 154(b) by 86 days.

This patent is subject to a terminal disclaimer.

(21) Appl. No.: 18/295,384

(22) Filed: Apr. 4, 2023

(65) Prior Publication Data

US 2023/0383236 A1    Nov. 30, 2023

Related U.S. Application Data

(63) Continuation of application No. 17/688,115, filed on Mar. 7, 2022, now Pat. No. 11,667,882, which is a continuation of application No. 17/153,062, filed on Jan. 20, 2021, now abandoned.

(60) Provisional application No. 62/963,306, filed on Jan. 20, 2020.

(51) Int. Cl.
*C12M 1/36* (2006.01)
*C12M 1/00* (2006.01)
*C12M 1/34* (2006.01)
*C12Q 1/00* (2006.01)
*C12Q 1/02* (2006.01)

(52) U.S. Cl.
CPC ............ *C12M 41/48* (2013.01); *C12M 29/10* (2013.01); *C12M 41/12* (2013.01); *C12M 41/26* (2013.01); *C12M 41/32* (2013.01); *C12M 41/34* (2013.01); *C12M 41/36* (2013.01); *C12M 41/44* (2013.01); *C12Q 1/00* (2013.01); *C12Q 1/02* (2013.01)

(58) Field of Classification Search
None
See application file for complete search history.

(56) References Cited

U.S. PATENT DOCUMENTS

| | | | |
|---|---|---|---|
| 4,978,616 A | 12/1990 | Dean et al. | |
| 5,994,129 A | 11/1999 | Armstrong et al. | |
| 6,607,910 B1 | 8/2003 | Dimitrijevich et al. | |
| 6,670,169 B1 | 12/2003 | Schob et al. | |
| 7,348,175 B2 | 3/2008 | Vilendrer et al. | |
| 7,981,668 B2 | 7/2011 | Wilkes et al. | |
| 8,492,140 B2 | 7/2013 | Smith et al. | |
| 8,835,159 B2 | 9/2014 | Harvey et al. | |
| 8,841,122 B2 | 9/2014 | Antwiler | |
| 8,951,784 B2 | 2/2015 | Gould et al. | |
| 9,399,755 B2 | 7/2016 | Karerangabo et al. | |
| 9,499,780 B2 | 11/2016 | Smith et al. | |
| 9,534,195 B2 | 1/2017 | Smith et al. | |
| 9,701,932 B2 | 7/2017 | Smith et al. | |
| 9,783,768 B2 | 10/2017 | Larcher et al. | |
| 10,723,986 B2 | 7/2020 | Smith et al. | |
| 10,844,338 B1 | 11/2020 | Smith et al. | |
| 2008/0274494 A1 | 11/2008 | Kertz | |
| 2009/0215104 A1 | 8/2009 | Taboas et al. | |
| 2010/0203638 A1 | 8/2010 | Adachi et al. | |
| 2014/0030768 A1 | 1/2014 | Medoff | |
| 2016/0032238 A1 | 2/2016 | Lawin et al. | |
| 2017/0096627 A1 | 4/2017 | Smith et al. | |
| 2017/0101618 A1 | 4/2017 | Kamen et al. | |
| 2017/0145365 A1 | 5/2017 | Nozaki et al. | |
| 2017/0198246 A1 | 7/2017 | Niazi | |
| 2018/0057783 A1 | 3/2018 | Paldus et al. | |
| 2019/0211294 A1 | 7/2019 | Kamieli | |
| 2019/0218501 A1 | 7/2019 | Kamen et al. | |

OTHER PUBLICATIONS

Lonza Complaint, 39 pages (2020).
Memorandum Opinion, 23 pages (2022).
Shi et al., "Performance of Mammalian Cell Culture Bioreactor with a New Impeller Design," Biotechnology and Bioengineering, vol. 40, pp. 260-270 (1992).
Legmann, Rachel, et al., "A predictive high-throughput scale-down model of monoclonal antibody production in CHO cells,k" Biotechnology and bioengineering 104.6; 1107-1120 (2009).
Michi, Johanna, Kyung Chan Park, and Pawel Swietach, "Evidence-based guidelines for controlling pH in mammalian live-cell culture systems," Communications biology 2.1, 1-12 (2019).
Goudar, Chetan T., James M. Piret, and Konstantinov B. Konstantinov, "Estimating cell specific oxygen uptake and carbon dioxide production rates for mammalian cells in perfusion culture," Biotechnology progress 27.5, 1347-1357 (2011).

*Primary Examiner* — Robert J Yamasaki
(74) *Attorney, Agent, or Firm* — Greenberg Traurig, LLP (57) ABSTRACT

Bioreactor systems and controlled operation of bioreactor systems are disclosed herein. The bioreactor systems can include at least one bioreactor chamber, at least one reservoir, a plurality of sensors, and a fluid circuit. The operational methods disclosed herein are directed towards growing cells or tissue while measuring various parameters, and a controlled operation of the various parameters during the operation of the bioreactor systems. The controlled operation of the parameters includes, for example, cell concentration; a rate of flow; a volume; a pH; a temperature; a level of oxygen; a level of carbon dioxide; a level of bicarbonate ion; nutrient compound; and any combination thereof.

20 Claims, 8 Drawing Sheets

DEVICE AND METHOD FOR CONTROLLING A BIOREACTOR

TECHNICAL FIELD

The present disclosure generally relates to bioreactor system configured for one or more control schemes of a bioreaction.

BACKGROUND ART

Generally, bioreactors may be used to culture microorganisms and living cells in a contained and controlled environment. Generally, culturing and processing of such microorganisms and cells may require several steps and the various steps may be performed before and/or during the culturing while monitoring certain parameters.

SUMMARY OF INVENTION

Growing various and specific cells or tissue in a bioreactor can be a challenge. The present disclosure generally relates to bioreactor systems and control schemes for bioreactor systems.

In some embodiments, the methods disclosed herein comprises operating the at least one reservoir, the at least one bioreactor and a plurality of pumps, wherein the operating comprises growing the plurality of cells in the at least one bioreactor; measuring, by the plurality of sensors, at least three parameters in the at least one bioreactor to obtain measured values for the at least three parameters, wherein the at least three parameters are selected from: a level of cell concentration of the plurality of cells; a rate of flow of the first liquid of the first medium of the at least one bioreactor into the reservoir chamber of the at least one reservoir; a rate of flow of the second fluid of the second medium from the at least one reservoir chamber into the bioreactor chamber of the at least one bioreactor; a level of the at least one first gas in the first medium; a level of the at least one first nutrient in the first medium; the first volume of the first fluid of the first medium; the first pH of the first fluid of the first medium; the first temperature of the first fluid of the first medium; or any combination thereof; providing a set point for each of the at least three parameters of the at least one bioreactor, wherein the set point corresponds to predetermined range of levels of the at least three parameters and comparing the measured values of the at least three parameters with the predetermined levels of the at least three parameters; simultaneously controlling the at least three parameters, until each measured value of the at least three parameters equals the predetermined levels of the at least three parameters by, at least adjusting the first volume of the first fluid wherein the plurality of pumps and the at least one reservoir are configured to remove at least some of the first fluid from the bioreactor or to add at least some of the second fluid to the first fluid such that the volume of the first fluid is adjustable.

In some embodiments disclosed herein, the bioreactor system comprises: at least one bioreactor chamber, at least one reservoir, a plurality of sensors, and a fluid circuit. In some embodiments, the fluid circuit comprises: a first section of the fluid circuit, wherein the first section fluidly connects the bioreactor chamber to the at least one reservoir, and is configured to flow a first fluid contained in the bioreactor chamber to the at least one reservoir, and a second section of the fluid circuit, wherein the second section fluidly connects the at least one reservoir to the bioreactor chamber, and is configured to flow a second fluid contained in the at least one reservoir to the bioreactor chamber.

In some embodiments disclosed herein, the methods disclosed herein comprises operating a bioreactor system. In some embodiments, operating the bioreactor system comprises: obtaining sensor measured values for at least three parameters via the plurality of sensors; and providing a predetermined setpoint for each of the at least three parameters. In some embodiments, obtaining and the providing can be in any sequential order. In some embodiments, the obtaining and the providing is performed in a specific sequential order. In some embodiments, the obtaining is performed prior to the providing. In some embodiments, the providing is performed prior to the obtaining. In some embodiments, after the obtaining and the providing, the method further comprises comparing the sensor measured values to the predetermined setpoint for the at least three parameters; and controlling the fluid circuit to: remove some of the first fluid from the bioreactor chamber, add some of the second fluid to the bioreactor chamber, or a combination thereof, until each of the sensor measured values substantially matches the predetermined setpoint of the at least three parameters.

In some embodiments disclosed herein, the bioreactor system comprises: the bioreactor system comprises: a bioreactor chamber, and a plurality of reservoirs, wherein the plurality of reservoirs comprises: a first reservoir, and a second reservoir. In some embodiments of the bioreactor system, the system further comprises a plurality of sensors, and a fluid circuit, wherein the fluid circuit comprises: a first section of the fluid circuit, wherein the first section fluidly connects the bioreactor chamber to the first reservoir, and is configured to flow a first fluid contained in the bioreactor chamber to the first reservoir, and a second section of the fluid circuit, wherein the second section fluidly connects the second reservoir to the bioreactor chamber, and is configured to flow a second fluid contained in the second reservoir to the bioreactor chamber.

In some embodiments of the methods disclosed herein, the method comprises: operating a bioreactor system, wherein the operating comprises: obtaining sensor measured values for at least three parameters via the plurality of sensors; providing a predetermined setpoint for each of the at least three parameters; comparing the sensor measured values to the predetermined setpoint for the at least three parameters; and controlling the fluid circuit. In some embodiments, the controlling the fluid circuit comprises: remove some of the first fluid from the bioreactor chamber, add some of the second fluid to the bioreactor chamber, or a combination thereof, until each of the sensor measured values substantially matches the predetermined setpoint of the at least three parameters.

In some embodiments, the at least three parameters are selected from: a level of cell concentration contained in the bioreactor chamber; a rate of flow of a first fluid into the at least one reservoir; a rate of flow of a second fluid into the bioreactor chamber; a volume of the first fluid; a pH of the first fluid; a temperature of the first fluid; a level of dissolved oxygen of the first fluid; a level of dissolved $CO_2$ in the first fluid; a level of $HCO_3$ in the first fluid; and a level of nutrient in the first fluid. In some embodiments, the level of nutrient includes an amount or concentration of the nutrient. In some embodiments, the nutrient includes at least one of Glucose, Lactate, Glutamine, Glutamate, or any combination thereof. In some embodiments, the nutrient includes Glucose, but does not include Lactate, Glutamine, and Glutamate. In some embodiments, the nutrient includes Lactate, but not Glucose, Glutamine, and Glutamate. In some embodiments, the nutrient includes Glutamine, but not Glucose, Lactate, and Glutamate. In some embodiments, the nutrient includes Glutamate, but not Glucose, Lactate, and Glutamine.

In some embodiments, the bioreactor system comprises a plurality of cells contained in the bioreactor chamber. In some embodiments, the first fluid is a liquid, a gas, a nutrient, a medium, or a combination there of. In some embodiments, the second fluid is a liquid, a gas, a nutrient, a medium, or a combination there of.

In some embodiments, controlling the fluid circuit comprises: adjusting one to three of the at least three parameters, wherein the fluid circuit adjusts automatically to the adjusting of the one to three of the at least three parameters.

In some embodiments, controlling the fluid circuit comprises: adjusting all of the at least three parameters, wherein the fluid circuit adjusts automatically to the adjusting all of the at least three parameters. In some embodiments, the adjusting is simultaneous.

In some embodiments, the operating of the bioreactor system is performed for a sufficient amount of time, to obtain a fold expansion of the plurality of cells of 1.5 to 10,000. In some embodiments, the operating of the bioreactor system is performed for a sufficient amount of time, to obtain a fold expansion of the plurality of cells of 100 to 7,500. In some embodiments, the operating of the bioreactor system is performed for a sufficient amount of time, to obtain a fold expansion of the plurality of cells of 500 to 2,500. In some embodiments, the operating of the bioreactor system is performed for a sufficient amount of time, to obtain a fold expansion of the plurality of cells of 50 to 1,000.

In some embodiments, the bioreactor system is configured to have at least two culturing modes selected from: a recirculation culturing mode, a perfusion culturing mode, a batch culturing mode, and a fed batch culturing mode. In some embodiments of the methods disclosed herein, operating the bioreactor system comprises changing, from one to another, of the at least two culturing modes.

In some embodiments of bioreactor systems disclosed herein, the system comprises: at least one bioreactor chamber; at least one reservoir; a plurality of sensors, a first controlled fluid flow path, wherein the first controlled fluid flow path is connected to the bioreactor chamber and to the at least one reservoir, and wherein the first controlled fluid flow path being configured for flowing fluid from the at least one reservoir to the bioreactor chamber; a second controlled fluid flow path, wherein the second controlled fluid flow path is connected to the bioreactor chamber and to the at least one reservoir, and wherein the second controlled fluid flow path being configured for flowing fluid from the bioreactor chamber to the at least one reservoir; and a control device. In some embodiments, the control device is in communication with the plurality of sensors, and is configured to receive a plurality of parameters from the plurality of sensors, wherein the control device is configured to automatically control the first controlled fluid flow path, the second controlled fluid flow path, or both based on the plurality of parameters received from the plurality of sensors.

In some embodiments of the bioreactor systems, the plurality of parameters includes at least three selected from: a level of cell concentration contained in the bioreactor chamber; a rate of flow of a first fluid into the at least one reservoir; a rate of flow of a second fluid into the bioreactor chamber; a volume of the first fluid; a pH of the first fluid; a temperature of the first fluid; a level of dissolved oxygen of the first fluid; a level of dissolved $CO_2$ in the first fluid; a level of $HCO_3$ in the first fluid; and a level of nutrient in the first fluid. In some embodiments, the level of nutrient includes an amount or concentration of the nutrient. In some embodiments, the nutrient includes at least one of Glucose, Lactate, Glutamine, Glutamate, or any combination thereof. In some embodiments, the nutrient includes Glucose, but does not include Lactate, Glutamine, and Glutamate. In some embodiments, the nutrient includes Lactate, but not Glucose, Glutamine, and Glutamate. In some embodiments, the nutrient includes Glutamine, but not Glucose, Lactate, and Glutamate. In some embodiments, the nutrient includes Glutamate, but not Glucose, Lactate, and Glutamine.

In some embodiments, the bioreactor system is configured to operate for a sufficient amount of time, to obtain a fold expansion of cells of 1.5 to 10,000. In some embodiments, the bioreactor system is configured to operate for a sufficient amount of time, to obtain a fold expansion of cells of 100 to 7,500. In some embodiments, the bioreactor system is configured to operate for a sufficient amount of time, to obtain a fold expansion of cells of 500 to 2,500. In some embodiments, the bioreactor system is configured to operate for a sufficient amount of time, to obtain a fold expansion of cells of 50 to 1,000.

In some embodiments, the bioreactor system is configured to have at least two culturing modes selected from: a recirculation culturing mode; a perfusion culturing mode; a batch culturing mode; and a fed batch culturing mode. In some embodiments, the bioreactor system is configured to change modes from one of the at least two culturing modes to another of the at least two culturing modes. In some embodiments, the bioreactor system includes a control device which is configured to change modes from one of the at least two culturing modes to another of the at least two culturing modes while in operation.

In some embodiments, the method is performed and wherein the operating is for a sufficient amount of time, to obtain a fold expansion of the plurality of cells of 1.5 to 10,000.

The embodiments disclosed herein can result in various improved results as shown below and described herein.

BRIEF DESCRIPTION OF DRAWINGS

Various embodiments of the present disclosure can be further explained with references to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as necessarily limiting, but merely as representative basis for teaching one skilled in the art to variously employ one or more illustrative embodiments.

DESCRIPTION OF EMBODIMENTS

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "fluid" refers to a liquid or a gas. As used herein, the term "medium" refers to a fluid or combination of fluids in which cells are capable of growing. As used herein, the term "flow" or "flows" refers to fluid that continually deforms under an applied pressure and/or an applied shear stress. Further to this, "a flow rate" as used herein is the rate per amount a time that a substance flow. Also, as used herein, the flow or movement of a substance entering the system (inlet), exiting the system (outlet) and pumps between parts in an exemplary bioreactor system are by any suitable one-way valve that allows the transfer of a substance. As used herein, when two chambers are "fluidly connected," this means that fluid is capable of flowing back and forth between the two chambers. Further, the term "fluidly connected" can also mean, based on some configurations of some embodiments, that fluid can have directional flow in a particular direction (e.g., from one chamber to another chamber).

As used herein, "feeding of cells" or "cell feeding" refers to introducing material to a bioreactor, where the introduced material facilitates cell growth. As used herein, "waste medium", "waste product" or "spent waste" is any material secreted by the cells during cell growth that if present in a cell medium, would hinder cell growth.

As used herein, "a batch culturing mode" refers to feeding a bioreactor system with a predetermined amount of medium and the cells using this fresh or new medium. The waste created by this mode of culturing may be expended at the same rate as receiving new medium and a batch mode is completed when all the medium is spent to waste. Recirculation is not done in a batch culture mode.

As used herein, "a fed batch culture mode" is the same as the batch culture mode, however after each cycle where all the fresh medium was spent, new medium is introduced. The cycle continues for a predetermined amount of times. Recirculation is not done in fed batch culture mode.

As used herein, "a perfusion culture mode" refers to equivalent volumes of fluid medium simultaneously fed and removed from a bioreactor system while cells are retained in the bioreactor chamber. This culture mode is constant feeding and constant removal of cell waste product.

As used herein, "a recirculation culture mode" refers to the continuous operation of a bioreactor and the medium circulates between two chambers only.

As used herein, "setpoint" or "setpoints" is a measured state a control system is aiming to reach and the control system changes parameters to meet a setpoint or a range for a setpoint.

As used herein, "level" or "levels" is a value or a range of values. For example, a "pH level" can mean a particular and specific pH value or a particular pH range.

In the present disclosure, some embodiments relate to a cell culturing processing and manipulation system including bioreactors and bioreactor systems designed for culturing of cells. In some embodiments, an exemplary bioreactor system may be configured to continuously allow all the necessary steps of selecting, culturing, modifying, activating, expanding, washing, concentrating and formulating in one single unit. In some embodiments, the exemplary bioreactor system may regulate various chemical parameters as needed for culturing cells. According to some embodiments, the exemplary bioreactor system may be used in a variety of culturing modes, such as but not limited to, a batch mode, a fed batch mode, a perfusion mode a recirculation mode, or any combination thereof. In some embodiments, the exemplary bioreactor system may be fully controlled in a closed, aseptic environment and may be implemented for a single use (to be disposed after one culturing cycle) as well as for multiple cycle uses.

In some embodiments, any products of the cells in an exemplary bioreactor system may be collected, including, but not limited to, secreted factors (e.g., exosomes, growth factors such as FGF, PDGF, and cytokines such as IL2, TNFalfa), proteins, peptides, antibiotics or amino acids. In some embodiments, an exemplary bioreactor system may provide for optimal and adaptive culturing, wherein manipulation of cells may be performed in a closed system, and wherein the manipulation can be automated. In some embodiments, the high growth density achieved in the exemplary bioreactor system may be 2-fold than that observed using standard culturing conditions. In some embodiments, the high growth density achieved in the exemplary bioreactor system may be 5-fold than that observed using standard culturing conditions. In some embodiments, the high growth density achieved in the exemplary bioreactor system may be greater than 10-fold observed using standard culturing conditions.

Figure 1:
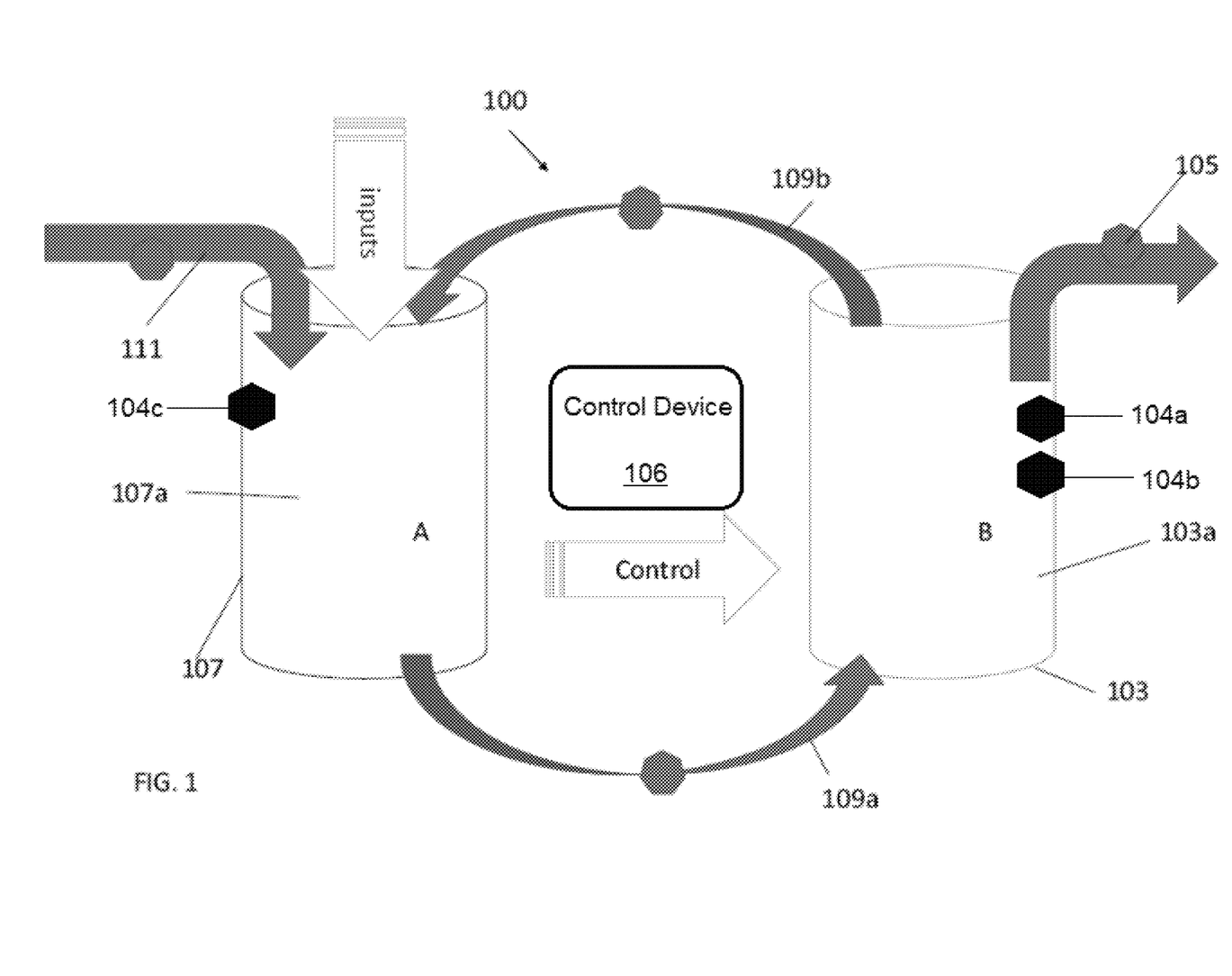
FIG. 1 is a schematic block diagram illustrating various components of a bioreactor system in accordance with some embodiments of the bioreactor systems of the present disclosure.

FIG. 1 schematically illustrates an exemplary bioreactor system 100 of the present disclosure. In some embodiments exemplary bioreactor system has a bioreactor 103 which may also comprise an outlet 105. In some embodiments a reservoir 107 is fluidly connected to bioreactor 103 by a fluid circuit (for example, a pump system) comprising at least two sections (e.g., two pumps 109a and 109b). The fluid circuit of the exemplary bioreactor system comprises at least two sections, each, for example, configured with a pump (109a, 109b), and the fluid circuit or the pump system generically will be referred to hereinafter as 109. In some embodiments, the reservoir 107 may further comprise an inlet 111. In some embodiments, the reservoir 107 may be another chamber with fluid medium. In some embodiments, the fluid medium in the reservoir may be the same as the fluid medium in the bioreactor. In some embodiments the fluid medium in the reservoir may be different than the fluid medium in the bioreactor. In some embodiments, the reservoir 107 does not contain any cells. In some embodiments, the reservoir is a container configured to contain a medium for providing delivery of a fluid to the bioreactor 103. In some embodiments, the reservoir is a container configured to receive and contain waste from the bioreactor 103. In some embodiments, the bioreactor system 100 includes at least two reservoirs, a first reservoir 107 configured to contain a medium for providing fluid to the bioreactor 103, wherein the fluid is received via the inlet 111; and a second reservoir (not shown in FIG. 1) configured to receive and contain waste from the bioreactor 103, via a fluid circuit (not shown in FIG. 1) or via the outlet 105.

In some embodiments of the exemplary bioreactor system, the bioreactor 103 further comprises an inner chamber 103a, where the inner chamber 103a is configured to contain at least a plurality of cells. In some embodiments, the bioreactor 103 comprises first fluid medium. In some embodiments, the first fluid medium may comprise at least one gas, at least one nutrient, wherein the at least one nutrient is present in a sufficient amount so as to feed the plurality of cells, a liquid, or any combination thereof. The liquid of the first fluid medium may further comprise a volume of the liquid in the bioreactor 103 In some embodiments, the liquid may have a temperature ranging from 37 Celsius to 42 Celsius. In some embodiments, the liquid may have a temperature ranging from 24 Celsius to 42 Celsius. In some embodiments, the liquid may have a pH level ranging from 6.5 pH to 7.5 pH. In some embodiments, the liquid may have a pH level ranging from 5 pH to 8 pH.

In some embodiments of the exemplary bioreactor system, the reservoir has an inner chamber 107a configured to contain at least a second fluid medium. The second fluid medium may comprise at least one gas, at least one nutrient in a sufficient amount to feed the at least a plurality of cells, a liquid, or any combination thereof. The liquid of the second medium may further comprise a volume of the liquid in the reservoir 107, a temperature and a pH level. Nutrients which may be used for culturing in an exemplary bioreactor system may include, but are not limited to, glucose, lactate, glutamine, glutamate, or a combination thereof. One or more gases that may be used for culturing in an exemplary bioreactor system may include, but are not limited to, oxygen, nitrogen, carbon dioxide, air, or any combination thereof. In some embodiments, the one or more gases are dissolved gases (e.g., dissolved in the medium).

The bioreactor 103, in some embodiments, may further comprise at least two sensors (not shown) configured to measure a plurality of parameters both physical and chemical in a fluid medium and cells contained in the bioreactor. In some embodiments, the bioreactor 103 may further comprise at least three sensors. In some embodiments, the bioreactor 103 may further comprise at least four sensors. In some embodiments, the bioreactor may comprise 5 or more sensors. In some embodiments, the reservoir 107 of the exemplary bioreactor system may contain at least one sensor (not shown) configured to measure parameters both physical and chemical in a fluid medium contained in the reservoir. In some embodiments, the reservoir 107 may further comprise at least 2 sensors. In some embodiments, the reservoir 107 may further comprise at least 3 sensors. In some embodiments, the reservoir 107 may further comprise at least 4 sensors. In some embodiments, the reservoir 107 may further comprise 5 or more sensors.

In some embodiments, the parameters sensed and measured in an exemplary bioreactor system (e.g., via sensors) may be selected from at least, but not limited to: a level of cell concentration; a level of the at least one nutrient; a level of at least one gas; a volume of liquid of the first medium; a pH level of a liquid of the first medium; a temperature of a liquid of the first medium; or any combination thereof.

In some embodiments, the parameters are sensed, detected, measured, controlled, or any combination thereof. In some embodiments of an exemplary bioreactor system, these parameters are selected from at least, but not limited to: a level of cell concentration contained in a bioreactor chamber; a rate of flow of a fluid into a reservoir; a rate of flow of the same or a different fluid into the bioreactor chamber; a volume of at least one fluid; a pH of at least one fluid; a temperature of at least one fluid; a level of dissolved oxygen of at least one fluid; a level of dissolved $CO_2$ in at least one fluid; a level of $HCO_3$ in at least one fluid; a level of nutrient in at least one fluid; and any combination thereof.

In some embodiments, the parameters sensed and measured may be, but are not limited to, a temperature, a pH level, a glucose concentration, dissolved oxygen concentration, lactate concentration, glutamine concentration, glutamate concentration, a concentration of dissolved carbon dioxide, a concentration of $HCO_3$ ions, and any combination thereof.

In some embodiments, at least three of the above parameters are detected by sensors of the bioreactor system. In some embodiments, at least three of the above parameters are measured by the bioreactor system. In some embodiments, at least three of the above parameters are controllable by the configuration of the bioreactor system (e.g., via a control device configured to control a fluid circuit). In some embodiments, an exemplary bioreactor system may control the parameters sensed and measured to a predetermined set point or a predetermined range of that measurement. In some embodiments, the exemplary bioreactor system may control 1 to 5 parameters. In some embodiments, the exemplary bioreactor may control 5 to 10 parameters. In some embodiments, the exemplary bioreactor may control at least three parameters simultaneously, substantially simultaneously, or the input of the control of multiple parameters is not simultaneous but the activation of the fluid circuit in the bioreactor system based on the input of the control does affect changes to these parameters simultaneously.

Returning to FIG. 1, the fluid circuit includes a fluid circuit 109 may be configured such that a first pump 109a extends from the reservoir 107 into the bioreactor 103; and a second pump 109b, extends into the at least one reservoir from the at least one bioreactor. In some embodiments, inlet 111 of reservoir 107 may be used to input materials for bioreactor cultures. In some embodiments outlet 105 of reservoir 107 may be used to remove spent waste, medium, or any combination thereof.

In some embodiments, this configuration of the fluid circuit (e.g., the pump system) 109, in an exemplary bioreactor system, results in the reservoir 107 controlling all of the inputs to the bioreactor via a control device or component thereto. In some embodiments, the reservoir 107 may control the parameters of the bioreaction or cells and a first fluid medium in the bioreactor using the unique pump system in conjunction with a reservoir. In some embodiments, the exemplary bioreactor system measures at least one parameter in the bioreactor and with that measurement may control that parameter by making changes to parameters in the reservoir. In some embodiments of the exemplary bioreactor system, the measurements of parameters are made in the bioreactor 103 and are controlled by making changes to parameters in the reservoir 107. In some embodiments, the exemplary bioreactor system may make changes to parameter or parameters in the reservoir to affect changes in the parameters in the bioreactor 103 by using the pump system 109. In some embodiments of the exemplary bioreactor system, the measurements of parameters are made in the bioreactor 103 and are only controlled by making changes to parameters in the reservoir 107. For example, in some embodiments, the pH level of the bioreactor first medium may be controlled to be at a range of 6.5 pH to 7.5 pH, by controlling the range of the reservoir fluid medium in a range of 5 pH to 8 pH while controlling other set points. In some embodiments, the following parameters, introduced by pump system 109 may also be measured by sensors in either the bioreactor or the reservoir: a rate of flow of liquid of the bioreactor into the reservoir, a rate of flow of liquid from the reservoir into the bioreactor, or any combination thereof.

In some embodiments, an exemplary bioreactor system may require more medium and nutrients and larger culturing volumes. In some embodiments, the exemplary bioreactor system may be configured to allow volume of the bioreactor to be varied and allow additional medium to be added without the need to transfer the cells to a separate container. In some embodiments, the exemplary bioreactor system may adjust volume of medium contained in the bioreactor with the pump system. In some embodiments, the pump system is configured to remove at least some of the liquid from the bioreactor, to add at least some of the reservoir liquid to bioreactor liquid such that the volume of the bioreactor liquid is adjustable, or any combination thereof.

In some embodiments, the exemplary bioreactor system may alternate between culturing modes, as detailed below. In some embodiments, alternating between the culturing modes may facilitate the ability of the bioreactor system to control a plurality of parameters simultaneously.

In some embodiments, the system comprises a batch culturing mode. In some embodiments, the exemplary bioreactor system may process in a batch culturing mode by the reservoir 107 accepting the predetermined amount of medium and pumping 102a the medium to the bioreactor. The bioreactor then may release waste product through outlet 105.

In some embodiments, the system comprises a fed batch culturing mode. In some embodiments, the exemplary bioreactor system may process a fed batch mode by the reservoir 107 accepting the predetermined amount of medium and pumping 102a this medium to the bioreactor. In some embodiments, the process is then repeated for a predetermined amount of time. In some embodiments, the predetermined amount of time is 1 day to two months. In some embodiments the predetermined amount of time is 2 days to 4 months.

In some embodiments, the system comprises a perfusion culture mode. In some embodiments, the exemplary bioreactor system may process a perfusion culture mode by the reservoir 107 accepting through inlet 111 medium and pumping 102a this same medium to the bioreactor. Sensors detect parameters so that only equivalent waste product is removed though outlet 105 of the bioreactor.

In some embodiments, the system comprises a recirculation mode. In some embodiments, the exemplary bioreactor system may process a recirculation culture mode by a fist pump 109a continually pumping the liquid medium from the reservoir to the bioreactor and a second pump 109b continually pumping the liquid medium from the bioreactor to the reservoir.

Figure 2A:
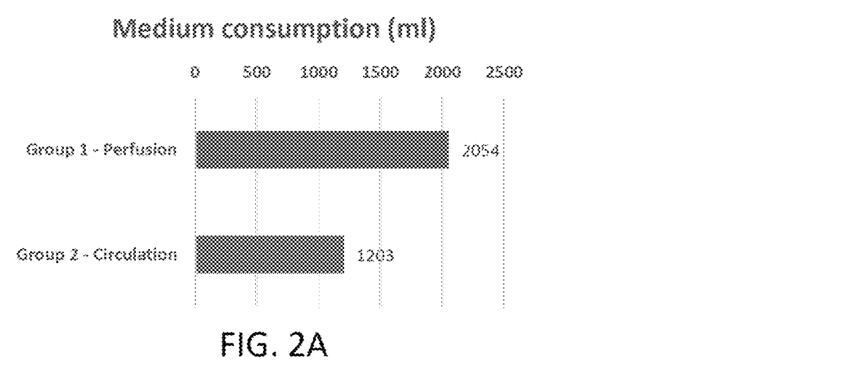
FIGS. 2A, 2B, and 2C are graphs demonstrating results of exemplary embodiments of the bioreactor control system of the current disclosure which are illustrative of some exemplary aspects of at least some embodiments of the present disclosure.
Figure 2B:
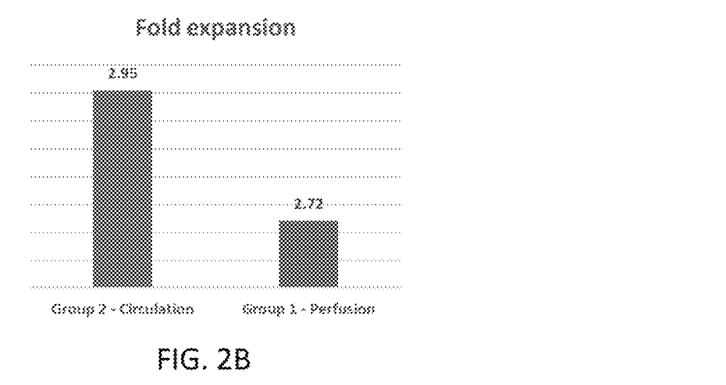
Figure 2C:
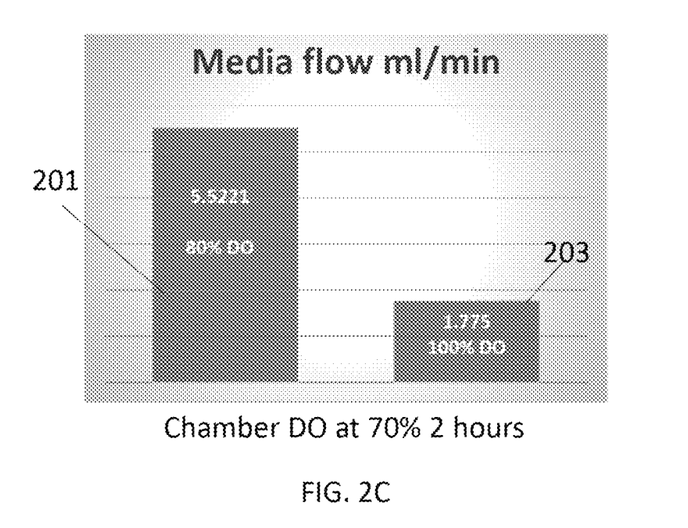

FIGS. 2A, 2B and 2C demonstrate, by way of specific non-limiting examples, cell growth in the same exemplary bioreactor system. For all the specific non-limiting examples of FIGS. 2A, 2B, and 2C, Group 1 is processed in perfusion mode and Group 2 is processed in a recirculation mode. Further, Group 1 is a four-day culture with eighty percent DO (dissolved Oxygen) in the bioreactor 103 and one hundred percent of DO in the reservoir 107. Group 1 seeding was $4.5 \times 10^7$ and harvest was $1.22 \times 10^8$. Group 2 is a four-day culture with eighty percent DO in bioreactor 103 and one hundred percent DO in the reservoir 107. Group 2 seeding was $4.5 \times 10^7$ and the harvest was $1.33 \times 10^8$.

FIG. 2A illustrates specific medium consumption in milliliters of the two groups. FIG. 2B illustrates the fold expansion of the two groups. FIG. 2C illustrates by non-limiting specific example, the controlling of a set point in the bioreactor first medium having more than one option of actions to maintain that set point. Here a setpoint of 70 percent DO for two hours in the bioreactor first medium was achieved by medium (media) from the reservoir being perfused into the bioreactor using pump 109a at a predetermined flow rate of milliliters minute and a predetermined DO percent level in the reservoir. Bar 201 is a flow rate of 5.5221 milliliters per minute with the reservoir at 80 percent DO. Bar 203 is a flow rate of 1.775 milliliters per minute with a 100 percent DO rate. The flexibility of the exemplary bioreactor system is illustrated by this experiment. The multiple options in the reservoir to control at least one same parameter in the bioreactors may be compared and utilized to design improved processes with for example lower sheer forces and efficient media use. In some embodiments, an improved process aimed at yielding high concentration of secreted factors and/or higher proliferations of cells or the correct phenotype while using efficient medium or resources. In some embodiments, the secreted factors such as exosomes can be collected via the wastes port once reading the correct density, parameters or time.

Figure 3A:
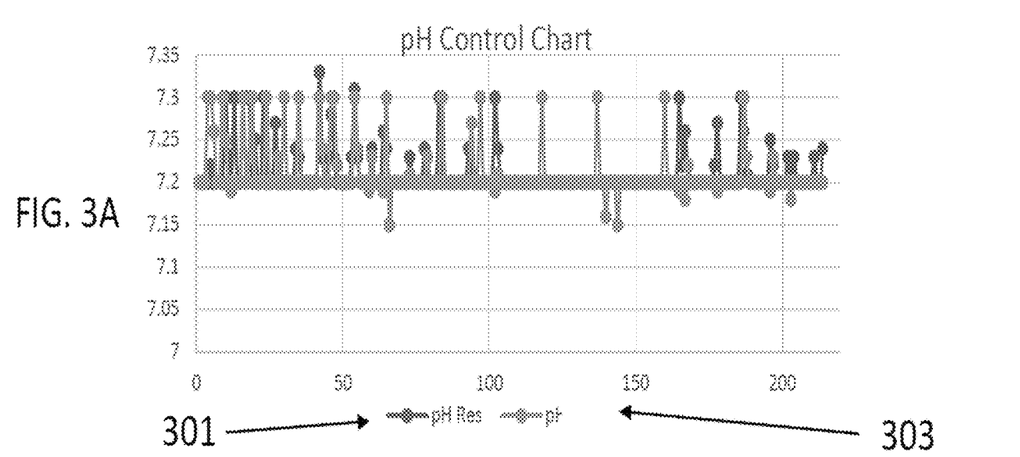
FIGS. 3A, 3B, 3C, and 3D are additional graphs demonstrating results of exemplary embodiments of the bioreactor control system of the current disclosure which are illustrative of some exemplary aspects of at least some embodiments of the present disclosure.
Figure 3B:
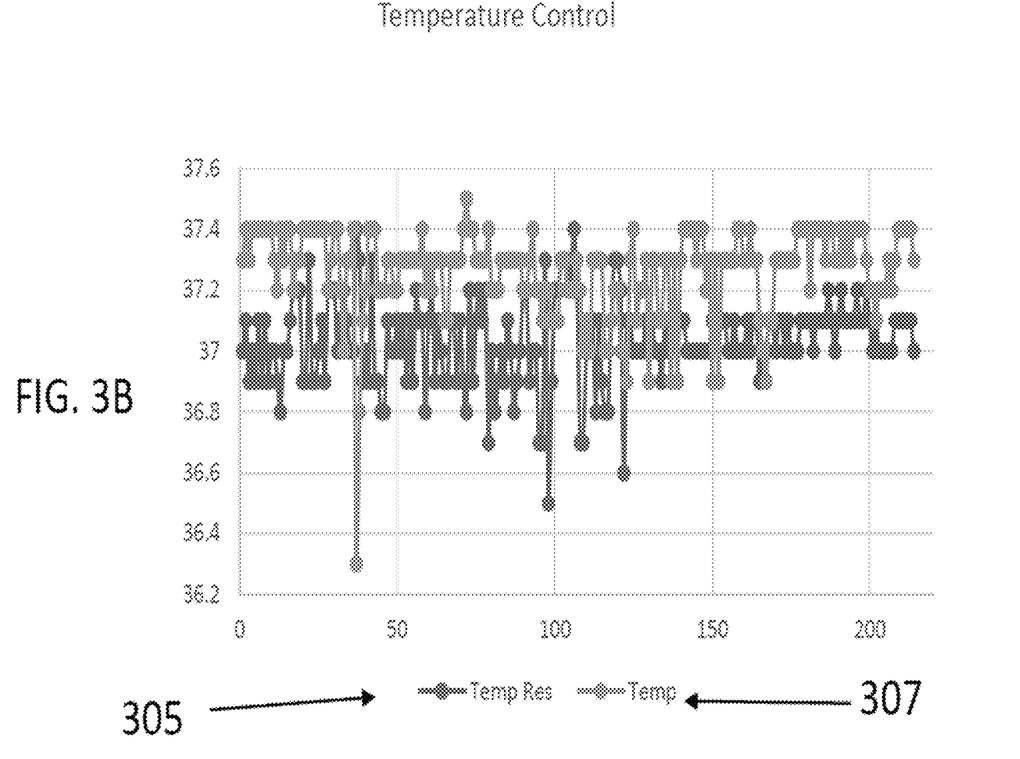
Figure 3C:
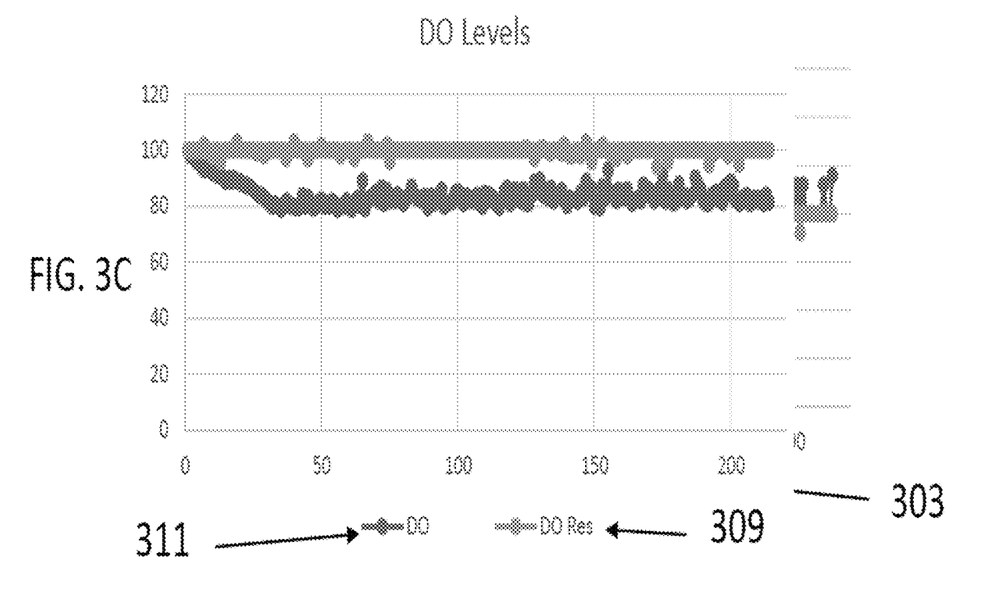
Figure 3D:
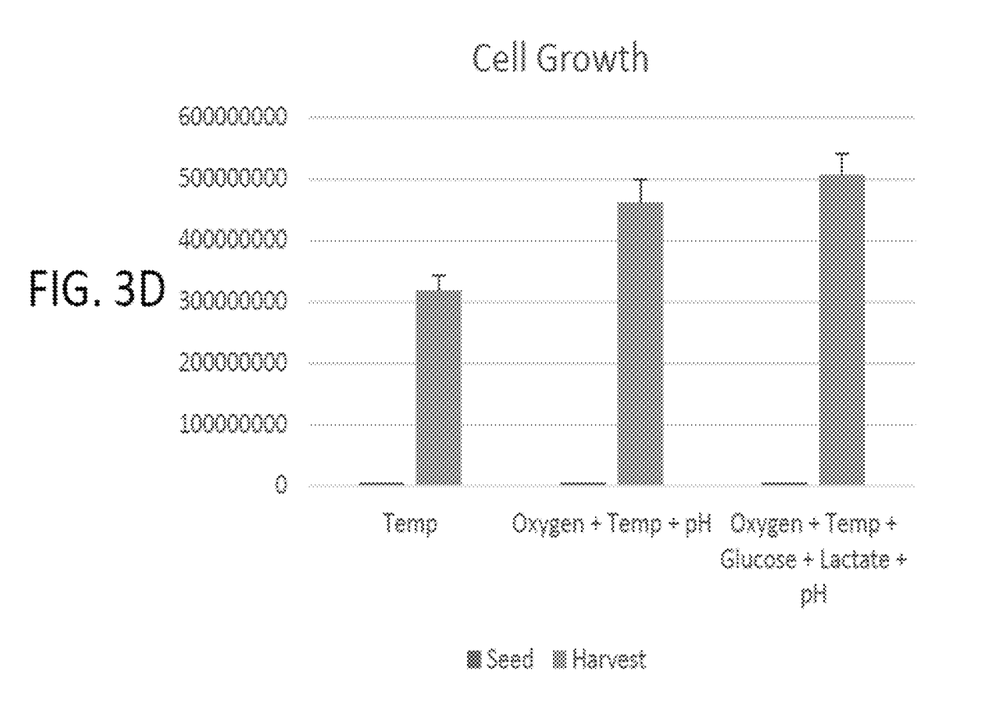

FIGS. 3A, 3B, 3C, and 3D show graphs that demonstrate by specific, non-limiting examples, various parameters that can be controlled in the exemplary bioreactor system. FIG. 3A compares the pH levels and control of the reservoir indicated by 301 with the pH levels in the bioreactor indicated by 303. FIG. 3B compares the temperature and control of the reservoir indicated by 305 with the temperature of the bioreactor indicated by 307. Similarly, FIG. 3C compares the DO levels and control of the reservoir indicated by 309 with the DO levels of the bioreactor indicated by 311. FIG. 3D illustrates by specific non-limiting example the cell growth from seed to harvest when controlling certain parameters that in this specific non-limiting example are: temperature alone; oxygen, temperature and pH level together; and oxygen, temperature, glucose, lactate and pH level together.

Figure 4:
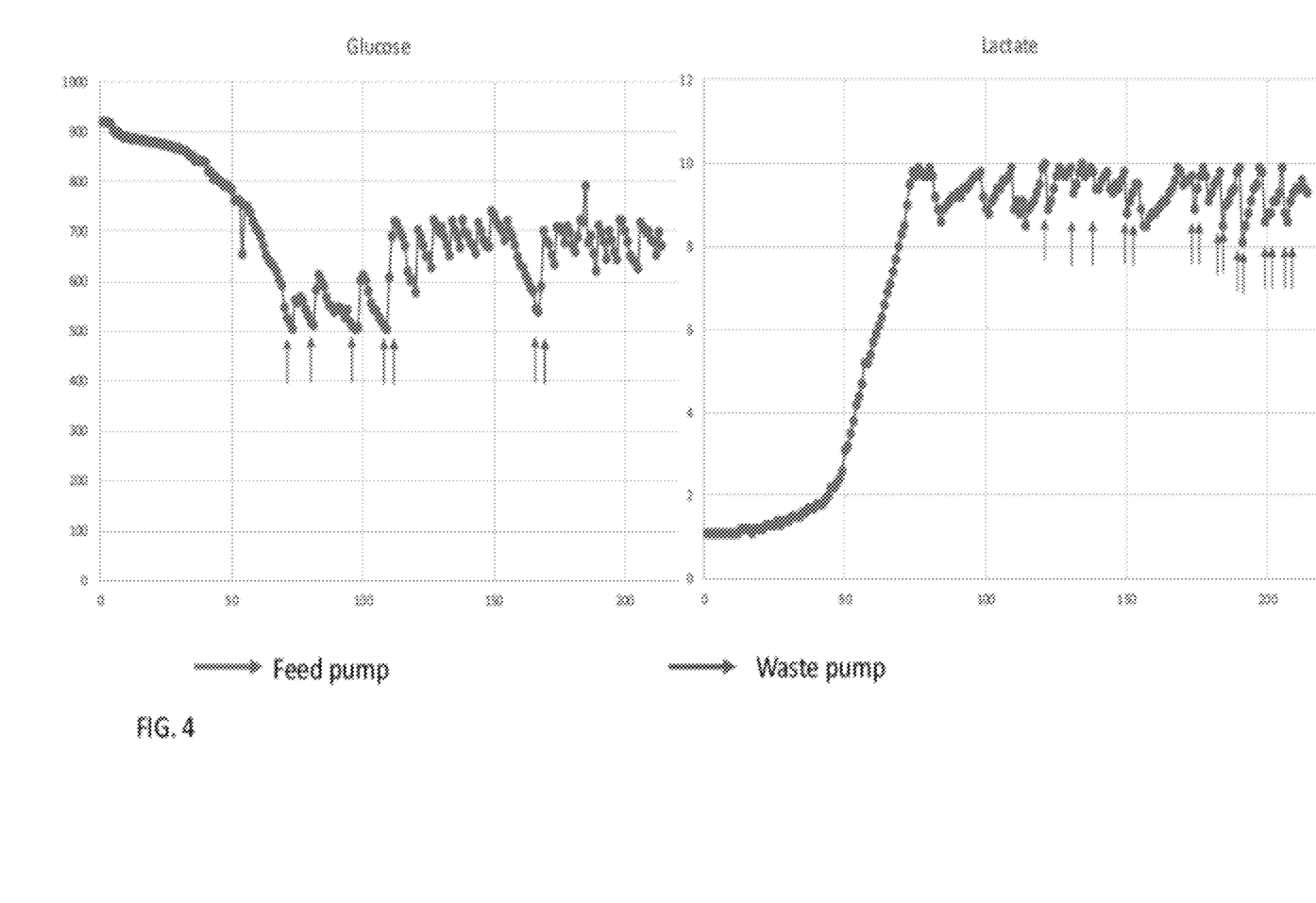
FIG. 4 is a schematic block diagram illustrating various components of a bioreactor system in accordance with some embodiments of the bioreactor systems of the present disclosure.

FIG. 4 shows timeline data graphs of yet another embodiment of an exemplary bioreactor system, where the glucose levels and the lactate levels are controlled simultaneously using a method of increasing volume of fluid in the bioreactor. In some embodiments, this method of control can result in more efficient use of medium as illustrated in the graphs of FIG. 4.

Figure 5:
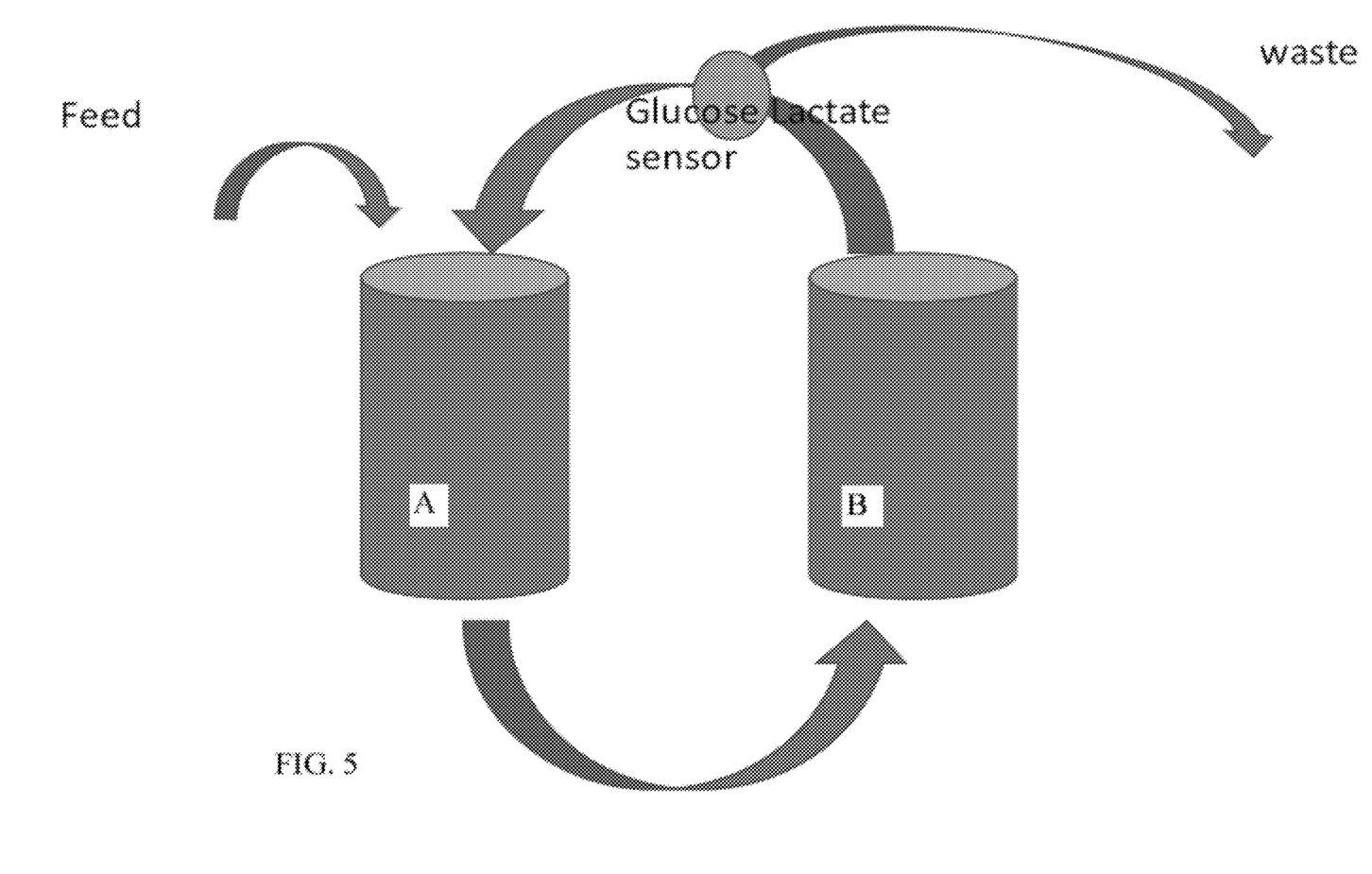
FIG. 5 is another schematic block diagram illustrating various components of a bioreactor system in accordance with some embodiments of the bioreactor systems of the present disclosure.

In an alternative embodiment, which is shown in FIG. 5, glucose and/or lactate levels are not measured in chamber A. Instead, glucose and/or lactate levels are only measured on the outlet of chamber B. Consequently, the media in A has a higher glucose level resulting in the media in chamber B at a lower level. In addition, the waste outlet (from B) and the fresh media in (A) is activated based only on the measurement of the media coming out of B.

Figure 6:
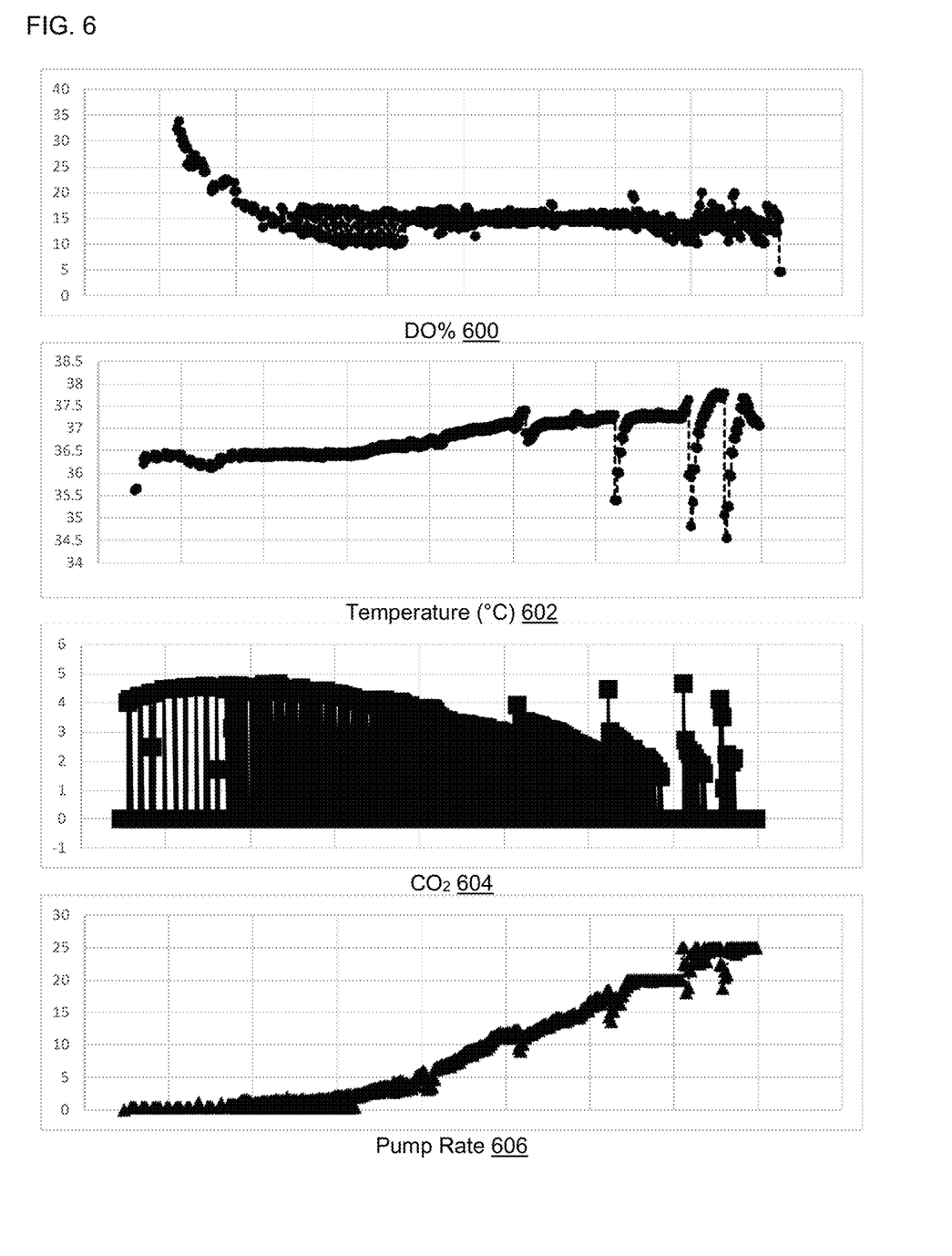
FIG. 6 shows graphs demonstrating results of exemplary embodiments of the bioreactor control system of the current disclosure which are illustrative of some exemplary aspects of at least some embodiments of the present disclosure.

FIG. 6 shows several timeline data graphs 600, 602, 604, 606 according to a particular experimental run using an embodiment of the bioreactor system, having been operated according to the embodiments of the control scheme and methods disclosed herein. In this example, various parameters were detected and measured: dissolved oxygen (DO) of the fluid in the bioreaction chamber; the temperature of the fluid in the bioreaction chamber; the pH of the fluid in the bioreaction chamber; the $CO_2$ levels of the fluid in the bioreaction chamber; and the flow rate of the fluid flowing into the bioreaction chamber. Over the operational timeline from which these data have been collected, cells contained in the bioreactor system grew. The DO graph (600) shows what happens over time when the setpoint for the DO is set at 15%. The temperature graph (602) shows the changes in the temperature in the bioreaction chamber over time. Also, as shown in graph (604), the $CO_2$ flow to the reservoir became lower, as there is less need for acid due to cell secretion of lactic acid in the reaction chamber, and there is an increased flow (606) from the reservoir to the reaction chamber over time. Accordingly, as evidenced by the results and data obtained and shown in these graphs, the flow rates, DO level, and $CO_2$ level in the reservoir can control and affect the DO and pH in the bioreaction chamber. Alternatively, it can be seen that, by controlling the setpoints for the various parameters (e.g., DO), the fluid circuit can be affected automatically to match the measured parameter to these setpoints (e.g., predetermined parameters). That is, it is possible to control, for example, the DO level in the bioreaction chamber by controlling (e.g., changing) the flow rates. Further, it is recognized that, over time, as there are more cells that are contained in the bioreaction chamber, the less $CO_2$ in needed in the reservoir due to increased flow rates and increased acid secretion.

Figure 7:
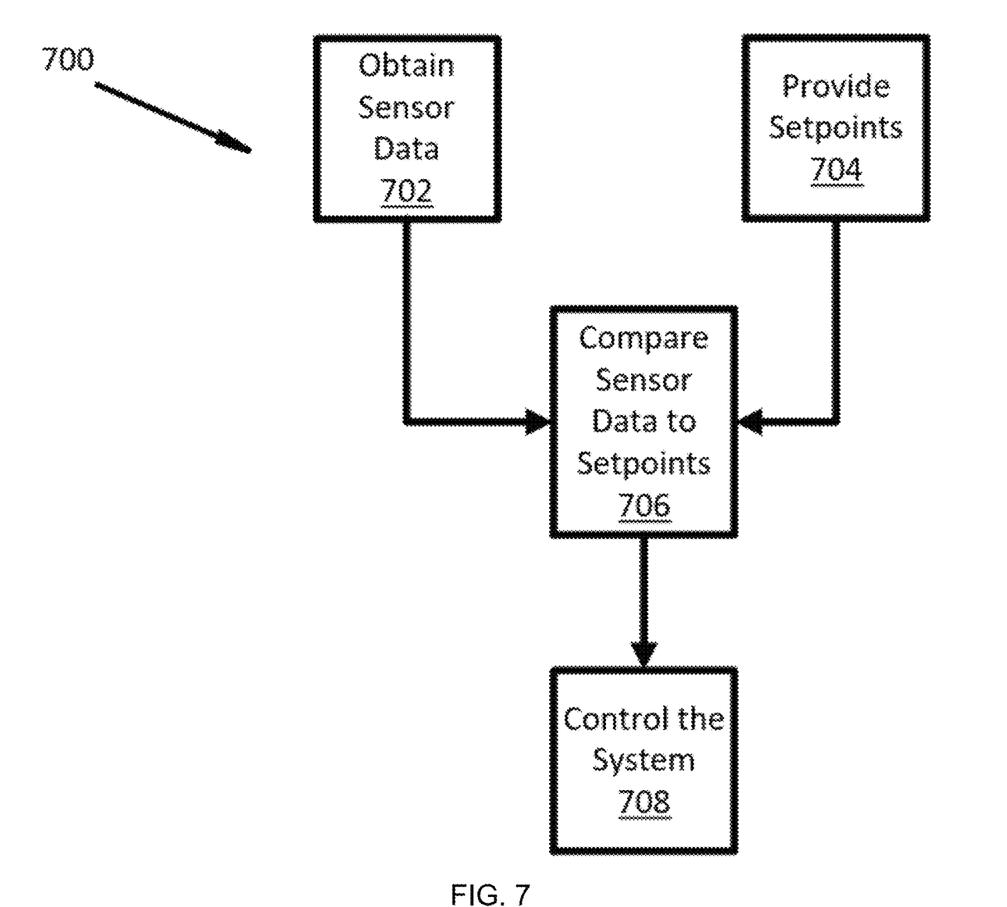
FIG. 7 is an exemplary flow chart of an embodiment of the methods disclosed herein.

FIG. 7 shows a flow chart of an embodiment of the methods disclosed herein. The embodiment of the method 700 comprises obtaining 702 sensor measured values for at least three parameters via the plurality of sensors. The method 700 also includes providing 704 a predetermined setpoint for each of the at least three parameters. In some embodiments, obtaining 702 and the providing 704 can be in any sequential order. In some embodiments, the obtaining 702 is performed before the providing 704 is performed. In some embodiments, the obtaining 702 is performed after the providing 704 is performed. In some embodiments, the obtaining 702 and the providing 704 are performed at or near the same time (i.e., simultaneously). Then, according to the embodiment shown in FIG. 7, the method 700 comprises comparing 706 the sensor measured values to the predetermined setpoint for the at least three parameters, and then controlling 708 the fluid circuit to: remove some of the first fluid from the bioreactor chamber, add some of the second fluid to the bioreactor chamber, or a combination thereof, until each of the sensor measured values substantially matches the predetermined setpoint of the at least three parameters. In some embodiments, other actions are taken to affect changes to the bioreactor system's operation based on the setpoints and the sensor measured values of the paramters.

The following Aspects recite the embodiments disclosed herein, of which any portion of any Aspect may be combined with any other portion of any Aspect.

Aspect 1. A method, comprising:
operating a bioreactor system,
wherein the bioreactor system comprises:
    a bioreactor chamber,
    at least one reservoir,
    a plurality of sensors, and
    a fluid circuit,
    wherein the fluid circuit comprises:
        a first section of the fluid circuit,
            wherein the first section fluidly connects the bioreactor chamber to the at least one reservoir, and is configured to flow a first fluid contained in the bioreactor chamber to the at least one reservoir, and
        a second section of the fluid circuit,
            wherein the second section fluidly connects the at least one reservoir to the bioreactor chamber, and is configured to flow a second fluid contained in the at least one reservoir to the bioreactor chamber;
wherein the operating the bioreactor system comprises:
    obtaining sensor measured values for at least three parameters via the plurality of sensors;
    providing a predetermined setpoint for each of the at least three parameters;
    comparing the sensor measured values to the predetermined setpoint for the at least three parameters; and
    controlling the fluid circuit to:
        remove some of the first fluid from the bioreactor chamber,
        add some of the second fluid to the bioreactor chamber, or
        a combination thereof,
        until each of the sensor measured values substantially matches the predetermined setpoint of the at least three parameters.

Aspect 2. The method of aspect 1, wherein the at least three parameters are selected from:
    a level of cell concentration contained in the bioreactor chamber;
    a rate of flow of a first fluid into the at least one reservoir;
    a rate of flow of a second fluid into the bioreactor chamber;
    a volume of the first fluid;
    a pH of the first fluid;
    a temperature of the first fluid;
    a level of dissolved oxygen of the first fluid;
    a level of dissolved $CO_2$ in the first fluid;
    a level of $HCO_3$ in the first fluid; and
    a level of nutrient in the first fluid.

Aspect 3. A method, comprising:
operating a bioreactor system,
wherein the bioreactor system comprises:
    a bioreactor chamber,
    a plurality of reservoirs,
    wherein the plurality of reservoirs comprises:
        a first reservoir, and
        a second reservoir,
    a plurality of sensors, and
    a fluid circuit,
    wherein the fluid circuit comprises:

a first section of the fluid circuit,
  wherein the first section fluidly connects the bioreactor chamber to the first reservoir, and is configured to flow a first fluid contained in the bioreactor chamber to the first reservoir, and
a second section of the fluid circuit,
  wherein the second section fluidly connects the second reservoir to the bioreactor chamber, and is configured to flow a second fluid contained in the second reservoir to the bioreactor chamber;
wherein the operating comprises:
  obtaining sensor measured values for at least three parameters via the plurality of sensors;
  providing a predetermined setpoint for each of the at least three parameters;
  comparing the sensor measured values to the predetermined setpoint for the at least three parameters; and
  controlling the fluid circuit to:
    remove some of the first fluid from the bioreactor chamber,
    add some of the second fluid to the bioreactor chamber, or a combination thereof,
    until each of the sensor measured values substantially matches the predetermined setpoint of the at least three parameters.

Aspect 4. The method of aspect 3, wherein the at least three parameters are selected from:
  a level of cell concentration contained in the bioreactor chamber;
  a rate of flow of a first fluid into the at least one reservoir;
  a rate of flow of a second fluid into the bioreactor chamber;
  a volume of the first fluid;
  a pH of the first fluid;
  a temperature of the first fluid;
  a level of dissolved oxygen of the first fluid;
  a level of dissolved $CO_2$ in the first fluid;
  a level of $HCO_3$ in the first fluid; and
  a level of nutrient in the first fluid.

Aspect 5. The method of any of aspects 1-4, wherein the bioreactor system comprises a plurality of cells contained in the bioreactor chamber.

Aspect 6. The method of any of aspects 1-5, wherein the first fluid is a liquid, a gas, a nutrient, a medium, or a combination there of.

Aspect 7. The method of any of aspects 1-6, wherein the second fluid is a liquid, a gas, a nutrient, a medium, or a combination there of.

Aspect 8. The method of any of aspects 1-7, wherein the controlling the fluid circuit comprises:
  adjusting one to three of the at least three parameters, wherein the fluid circuit adjusts automatically to the adjusting of the one to three of the at least three parameters.

Aspect 9. The method of any of aspects 1-7, wherein the controlling the fluid circuit comprises:
  adjusting all of the at least three parameters, wherein the fluid circuit adjusts automatically to the adjusting all of the at least three parameters.

Aspect 10. The method of aspect 9, wherein the adjusting is simultaneous.

Aspect 11. The method of any of aspects 1-10, wherein the operating the bioreactor system is performed for a sufficient amount of time, to obtain a fold expansion of the plurality of cells of 1.5 to 10,000.

Aspect 12. The method of any of aspects 1-10, wherein the operating the bioreactor system is performed for a sufficient amount of time, to obtain a fold expansion of the plurality of cells of 100 to 7,500.

Aspect 13. The method of any of aspects 1-10, wherein the operating the bioreactor system is performed for a sufficient amount of time, to obtain a fold expansion of the plurality of cells of 500 to 2,500.

Aspect 14. The method of any of aspects 1-10, wherein the operating the bioreactor system is performed for a sufficient amount of time, to obtain a fold expansion of the plurality of cells of to 1,000.

Aspect 15. The method of any of aspects 1-14,
  wherein the bioreactor system is configured to have at least two culturing modes selected from:
    a recirculation culturing mode,
    a perfusion culturing mode,
    a batch culturing mode, and
    a fed batch culturing mode; and
  the operating the bioreactor system further comprises:
    changing, from one to another, of the at least two culturing modes.

Aspect 16. A bioreactor system, comprising:
  a bioreactor chamber;
  at least one reservoir;
  a plurality of sensors,
  a first controlled fluid flow path,
    wherein the first controlled fluid flow path is connected to the bioreactor chamber and to the at least one reservoir, and
    wherein the first controlled fluid flow path being configured for flowing fluid from the at least one reservoir to the bioreactor chamber;
  a second controlled fluid flow path,
    wherein the second controlled fluid flow path is connected to the bioreactor chamber and to the at least one reservoir, and
    wherein the second controlled fluid flow path being configured for flowing fluid from the bioreactor chamber to the at least one reservoir; and
  a control device
    wherein the control device is in communication with the plurality of sensors, and is configured to receive a plurality of parameters from the plurality of sensors,
    wherein the control device is configured to control the first controlled fluid flow path, the second controlled fluid flow path, or both based on the plurality of parameters received from the plurality of sensors.

Aspect 17. The bioreactor system of aspect 16, wherein the plurality of parameters includes at least three selected from:
  a level of cell concentration contained in the bioreactor chamber;
  a rate of flow of a first fluid into the at least one reservoir;
  a rate of flow of a second fluid into the bioreactor chamber;
  a volume of the first fluid;
  a pH of the first fluid;
  a temperature of the first fluid;
  a level of dissolved oxygen of the first fluid;
  a level of dissolved $CO_2$ in the first fluid;
  a level of $HCO_3$ in the first fluid; and
  a level of nutrient in the first fluid.

Aspect 18. The bioreactor system of any of aspects 16-17, wherein the first fluid is a liquid, a gas, a nutrient, or a combination there of.

Aspect 19. The bioreactor system of any of aspects 16-17, wherein the second fluid is a liquid, a gas, a nutrient, or a combination there of.

Aspect 20. The bioreactor system of any of aspects 16-19, wherein the bioreactor system is configured to operate for a sufficient amount of time, to obtain a fold expansion of cells of 1.5 to 10,000.

Aspect 21. The bioreactor system of any of aspects 16-18, wherein the bioreactor system is configured to operate for a sufficient amount of time, to obtain a fold expansion of cells of 100 to 7,500.

Aspect 22. The bioreactor system of any of aspects 16-18, wherein the bioreactor system is configured to operate for a sufficient amount of time, to obtain a fold expansion of cells of 500 to 2,500.

Aspect 23. The bioreactor system of any of aspects 16-18, wherein the bioreactor system is configured to operate for a sufficient amount of time, to obtain a fold expansion of cells of 50 to 1,000.

Aspect 24. The bioreactor system of any of aspects 16-23, wherein the bioreactor system is configured to have at least two culturing modes selected from:
a recirculation culturing mode;
a perfusion culturing mode;
a batch culturing mode; and
a fed batch culturing mode.

Aspect 25. The bioreactor system of aspect 24, wherein the control device is configured to change modes from one of the at least two culturing modes to another of the at least two culturing modes.

Aspect 26. The bioreactor system of aspect 24, wherein the control device is configured to change modes from one of the at least two culturing modes to another of the at least two culturing modes while in operation.

Aspect 27. A method, comprising:
obtaining a bioreactor,
wherein the bioreactor comprises:
a bioreactor chamber,
wherein the bioreactor chamber is configured to contain at least:
a plurality of cells, and
a first medium,
wherein the first medium comprises one or more of:
a first liquid,
wherein the first liquid has a first volume, a first temperature, and a first pH,
a first gas, and
a first nutrient,
an outlet, and
a plurality of sensors;
obtaining a reservoir,
wherein the reservoir comprises:
an inlet, and
a reservoir chamber,
wherein the reservoir chamber is configured to contain a second medium,
the second medium comprises one or more of:
a second liquid,
wherein the second liquid has a second volume, a second temperature, and a second pH,
a second gas, and
a second nutrient;
obtaining a plurality of pumps,
wherein the plurality of pumps comprises:
a first pump, wherein the first pump extends from the reservoir to the bioreactor chamber, and
a second pump, wherein the second pump extends from the bioreactor to the reservoir;
operating the reservoir, the bioreactor, and the plurality of pumps,
wherein the operating comprises:
growing the plurality of cells in the bioreactor;
obtaining measured values for at least three parameters via the plurality of sensors, wherein the at least three parameters are selected from:
a level of cell concentration of the plurality of cells,
a rate of flow of the first liquid into the reservoir chamber of the reservoir,
a rate of flow of the second liquid into the bioreactor chamber,
an amount of the first gas,
an amount of the first nutrient,
the first volume,
the first pH, and
the first temperature;
providing a set point for each of the at least three parameters of the bioreactor;
wherein the set point corresponds to a predetermined range for each of the at least three parameters;
comparing the measured values to the predetermined range for each of the at least three parameters; and
controlling the at least three parameters simultaneously until each of the measured values is substantially within the predetermined range of the at least three parameters by adjusting the first volume via:
removing some of the first liquid from the bioreactor, or
adding some of the second liquid to the first liquid.

While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

What is claimed is:

1. A bioreactor system comprising:
a bioreactor chamber,
wherein the bioreactor chamber contains grown cells;
at least one sensor in the bioreactor chamber,
wherein the at least one sensor is configured to determine actual values of three parameters within the bioreactor chamber, the three parameters comprising:
a nutrient level within the bioreactor chamber,
a pH level within the bioreactor chamber, and
an $O_2$ level within the bioreactor chamber,
a reservoir,
wherein the reservoir does not contain any cells;
a first fluid circuit configured to permit flow of a first fluid from the bioreactor chamber to the reservoir;
a second fluid circuit configured to permit flow of a second fluid from the reservoir to the bioreactor chamber;
a controller configured to flow
a first liquid from the bioreactor chamber into the reservoir through the first fluid circuit, and
a second liquid from the reservoir into the bioreactor chamber through the second fluid circuit to adjust simultaneously each of the actual values of the parameters within the bioreactor chamber to match a corresponding set point value of the parameter, after determining that each of the set point values within the bioreactor chamber is not equal to the corresponding actual value; and a third fluid circuit configured to permit one-way flow of a waste product out of the bioreactor chamber, wherein the first fluid circuit, the second fluid circuit, and the third fluid circuit are fluidly isolated from one another.

2. The bioreactor system of claim 1, wherein the at least one sensor comprises a first sensor to measure the actual values of the nutrient level within the bioreactor chamber, the pH level within the bioreactor chamber, and the $O_2$ level within the bioreactor chamber.

3. The bioreactor system of claim 1, wherein the at least one sensor comprises a first sensor to measure the actual value of the nutrient level within the bioreactor chamber, a second sensor to measure the actual value of the pH level within the bioreactor chamber, and a third sensor to measure the actual value of the $O_2$ level within the bioreactor chamber.

4. The bioreactor system of claim 1, further comprising an outlet connected to the third fluid circuit.

5. The bioreactor system of claim 4,
wherein the outlet is configured to permit one-way flow of the waste product out of the third fluid circuit.

6. The bioreactor system of claim 5, further comprising:
an inlet, the inlet configured to flow the first fluid into the reservoir.

7. The bioreactor system of claim 6, wherein the inlet is fluidly isolated from the outlet.

8. The bioreactor system of claim 1, wherein the first fluid has a first nutrient level, a first pH level, and a first $O_2$ level,
wherein the second fluid has a second nutrient level, a second pH level, and a second $O_2$ level,
wherein the second nutrient level is different than the first nutrient level,
wherein the second pH level is different than the first pH level,
wherein the second $O_2$ level is different than the first $O_2$ level.

9. The bioreactor system of claim 1, wherein the first fluid circuit is configured to permit one-way flow in a first direction.

10. The bioreactor system of claim 9, wherein the second fluid circuit is configured to permit one-way flow in a second direction, wherein the first direction is different than the second direction.

11. A bioreactor system comprising:
a bioreactor chamber,
wherein the bioreactor chamber contains grown cells;
at least one sensor in the bioreactor chamber,
wherein the at least one sensor is configured to determine actual values of five parameters within the bioreactor chamber, the five parameters comprising:
a nutrient level within the bioreactor chamber,
a pH level within the bioreactor chamber,
an $O_2$ level within the bioreactor chamber,
a $CO_2$ level within the bioreactor chamber, and
an $HCO_3$ level within the bioreactor chamber;
a reservoir,
wherein the reservoir does not contain any cells;
a first fluid circuit configured to permit flow of a first fluid from the bioreactor chamber to the reservoir;

a second fluid circuit configured to permit flow of a second fluid from the reservoir to the bioreactor chamber;

a controller configured to flow
a first liquid from the bioreactor chamber into the reservoir through the first fluid circuit, and
a second liquid from the reservoir into the bioreactor chamber through the second fluid circuit to adjust simultaneously each of the actual values of the parameters within the bioreactor chamber to match a corresponding set point value of the parameter, after determining that each of the set point values within the bioreactor is not equal to the corresponding actual value; and a third fluid circuit configured to permit one-way flow of a waste product out of the bioreactor chamber, wherein the first fluid circuit, the second fluid circuit, and the third fluid circuit are fluidly isolated from one another.

12. The bioreactor system of claim 11, wherein the at least one sensor comprises a first sensor to measure the actual values of the nutrient level within the bioreactor chamber, the pH level within the bioreactor chamber, the $O_2$ level within the bioreactor chamber, the $CO_2$ level within the bioreactor chamber, and the $HCO_3$ level within the bioreactor chamber.

13. The bioreactor system of claim 11, wherein the at least one sensor comprises a first sensor to measure the actual value of the nutrient level within the bioreactor chamber, a second sensor to measure the actual value of the pH level within the bioreactor chamber, a third sensor to measure the actual value of the $O_2$ level within the bioreactor chamber, a fourth sensor to measure the $CO_2$ level within the bioreactor chamber, and a fifth sensor to measure the $HCO_3$ level within the bioreactor chamber.

14. The bioreactor system of claim 11, further comprising an outlet connected to the third fluid circuit.

15. The bioreactor system of claim 14,
wherein the outlet is configured to permit one-way flow of the waste product out of the third fluid circuit.

16. The bioreactor system of claim 15, further comprising:
an inlet, the inlet configured to flow the first fluid into the reservoir.

17. The bioreactor system of claim 16, wherein the inlet is fluidly isolated from the outlet.

18. The bioreactor system of claim 11, wherein the first fluid has a first nutrient level, a first pH level, a first $O_2$ level, a first $CO_2$ level, and a first $HCO_3$ level,
wherein the second fluid has a second nutrient level, a second pH level, a second $O_2$ level, a second $CO_2$ level, and a second $HCO_3$ level,
wherein the second nutrient level is different than the first nutrient level,
wherein the second pH level is different than the first pH level,
wherein the second $O_2$ level is different than the first $O_2$ level,
wherein the second $CO_2$ level is different that the first $CO_2$ level,
wherein the second $HCO_3$ level is different than the first $HCO_3$ level.

19. The bioreactor system of claim 11, wherein the first fluid circuit is configured to permit one-way flow in a first direction.

20. The bioreactor system of claim 19, wherein the second fluid circuit is configured to permit one-way flow in a second direction,
    wherein the first direction is different than the second direction.

\* \* \* \* \*